US011439988B2

(12) United States Patent
Schmidt

(10) Patent No.: US 11,439,988 B2
(45) Date of Patent: Sep. 13, 2022

(54) METHOD FOR MANUFACTURING CATALYSTS WITH REDUCED ATTRITION

(71) Applicant: W. R. GRACE & CO.-CONN., Columbia, MD (US)

(72) Inventor: Stephen R. Schmidt, Silver Spring, MD (US)

(73) Assignee: W. R. GRACE & CO.-CONN., Columbia, MD (US)

(*) Notice: Subject to any disclaimer, the term of this patent is extended or adjusted under 35 U.S.C. 154(b) by 19 days.

(21) Appl. No.: 16/462,717

(22) PCT Filed: Nov. 20, 2017

(86) PCT No.: PCT/US2017/062460
§ 371 (c)(1),
(2) Date: May 21, 2019

(87) PCT Pub. No.: WO2018/098053
PCT Pub. Date: May 31, 2018

(65) Prior Publication Data
US 2019/0366307 A1    Dec. 5, 2019

Related U.S. Application Data

(60) Provisional application No. 62/425,262, filed on Nov. 22, 2016.

(51) Int. Cl.
*B01J 23/755* (2006.01)
*B01J 25/02* (2006.01)
*B01J 35/00* (2006.01)
*B01J 35/02* (2006.01)
*B01J 37/06* (2006.01)
*C07C 29/17* (2006.01)
*C22B 3/00* (2006.01)

(52) U.S. Cl.
CPC ............ *B01J 23/755* (2013.01); *B01J 25/02* (2013.01); *B01J 35/002* (2013.01); *B01J 35/023* (2013.01); *B01J 37/06* (2013.01); *C07C 29/172* (2013.01); *C22B 23/0446* (2013.01)

(58) Field of Classification Search
CPC ........ B01J 23/755; B01J 25/02; B01J 35/002; B01J 35/023; B01J 37/06; B01J 23/85; B01J 23/883; B01J 25/00; C07C 29/172; C07C 29/132; C22B 23/0446
See application file for complete search history.

(56) References Cited

U.S. PATENT DOCUMENTS

| | | | | |
|---|---|---|---|---|
| 1,563,587 A * | 12/1925 | Raney | ...................... | B01J 25/02 502/301 |
| 1,628,190 A | 5/1927 | Raney | | |
| 1,915,473 A | 6/1933 | Raney | | |
| 2,094,117 A * | 9/1937 | Byrkit, Jr. | ................. | C09F 1/00 530/216 |
| 2,139,602 A | 12/1938 | Raney | | |
| 2,391,283 A * | 12/1945 | Peterson | ................... | C07C 5/10 585/270 |
| 2,461,396 A | 2/1949 | Raney | | |
| 2,673,189 A * | 3/1954 | Reynolds | ................. | B01J 25/00 502/301 |
| 2,950,260 A * | 8/1960 | Rosenbaum | ............ | B01J 25/02 502/335 |
| 2,977,327 A | 3/1961 | Raney | | |
| 3,676,364 A | 7/1972 | Coates | | |
| 3,781,227 A * | 12/1973 | Sokolsky et al. | ........ | B01J 25/02 502/301 |
| 4,032,193 A * | 6/1977 | Drinkard | ................. | E21B 43/24 299/4 |
| 4,153,578 A * | 5/1979 | De Thomas | ............ | B01J 25/02 502/200 |
| 4,247,722 A | 1/1981 | Kelley et al. | | |
| 4,826,799 A | 5/1989 | Cheng et al. | | |
| 4,864,066 A * | 9/1989 | Mueller | ................ | C07C 29/172 568/861 |
| 4,895,994 A | 1/1990 | Cheng et al. | | |
| 5,253,993 A | 10/1993 | Birkenstock et al. | | |
| 5,395,813 A | 3/1995 | Clavenna et al. | | |
| 5,554,573 A | 9/1996 | Cordier et al. | | |

(Continued)

FOREIGN PATENT DOCUMENTS

| | | | |
|---|---|---|---|
| CN | 1487911 A | 4/2004 | |
| CN | 1565731 A | 1/2005 | |

(Continued)

OTHER PUBLICATIONS

Extended (Supplementary) European Search Report dated Aug. 31, 2020, issued in counterpart EP Application No. 17873713.6. (18 pages).
Ivanov et al., "Raney nickel catalysts from mechanical Ni—Al alloys", Materials Letters, vol. 7, Issues 1-2, Aug. 1988, pp. 55-56.
Office Action dated Dec. 14, 2020, issued in counterpart IN Application No. 201917024571, with English Translation. (7 pages).
Office Action dated Jun. 29, 2021, issued in counterpart EP application No. 17 873 713.6. (15 pages).

(Continued)

*Primary Examiner* — Anthony J Zimmer
(74) *Attorney, Agent, or Firm* — Foley & Lardner LLP

(57) ABSTRACT

The present invention discloses an inventive method for manufacturing a catalyst using alloy granules having a high-Ni content. The inventive method may include providing alloy granules comprising aluminum and nickel, and treating the alloy granules with an alkaline solution to form the catalyst. A content of the nickel in the alloy granules may be within a range of about 43 wt % to about 60 wt %. The alloy granules may have effective diameters within a range of about 1 mm to about 10 mm. The catalyst may have an attrition value of less than about 7.0%.

12 Claims, 1 Drawing Sheet

(56) References Cited

U.S. PATENT DOCUMENTS

| | | | |
|---|---|---|---|
| 5,888,923 | A | 3/1999 | Chen et al. |
| 5,888,932 | A * | 3/1999 | Anderson ............. A01N 43/80 504/118 |
| 6,368,996 | B1 | 4/2002 | Mu et al. |
| 6,395,934 | B1 | 5/2002 | Wegener et al. |
| 6,486,366 | B1 | 11/2002 | Ostgard et al. |
| 7,375,053 | B2 | 5/2008 | Schmidt |
| 8,247,561 | B2 | 8/2012 | Marion |
| 2002/0019565 | A1 | 2/2002 | Berk et al. |
| 2002/0037808 | A1 | 3/2002 | Ostgard et al. |
| 2002/0106527 | A1 | 8/2002 | Schmidt |
| 2002/0151751 | A1 | 10/2002 | Ostgard et al. |
| 2003/0018224 | A1 | 1/2003 | Tsuji et al. |
| 2004/0074337 | A1 | 4/2004 | Venkatesan et al. |
| 2004/0137288 | A1 | 7/2004 | Morgenstern |
| 2006/0070918 | A1 | 4/2006 | Seapan et al. |
| 2007/0129242 | A1 | 6/2007 | Xu et al. |
| 2008/0015267 | A1 * | 1/2008 | Lu ........................... C10G 2/33 518/718 |
| 2008/0280756 | A1 * | 11/2008 | Biberger ............ B01J 37/0018 502/232 |
| 2009/0023582 | A1 | 1/2009 | Lacey et al. |
| 2009/0209412 | A1 | 8/2009 | Parent et al. |
| 2011/0230681 | A1 | 9/2011 | Letourneur et al. |
| 2015/0231612 | A1 | 8/2015 | Dai et al. |
| 2018/0169632 | A1 | 6/2018 | Dai et al. |
| 2018/0370884 | A1 * | 12/2018 | Vicente .................. B01J 27/236 |

FOREIGN PATENT DOCUMENTS

| | | | | |
|---|---|---|---|---|
| CN | 104945226 | A | | 9/2015 |
| EP | 163377881 | | | 12/2009 |
| GB | 633531 | A | | 12/1949 |
| GB | 1242358 | A | * 8/1971 | ............. B01J 25/02 |
| JP | S49-034964 | B1 | | 9/1974 |
| JP | H07-165682 | A | | 6/1995 |
| JP | 2004-526686 | A | | 9/2004 |
| JP | 2011192701 | A | * 9/2011 | |
| WO | 2005042153 | A1 | | 5/2005 |
| WO | WO-2014/023220 | A1 | | 2/2014 |

OTHER PUBLICATIONS

English translation of Taiwanese Office Action dated Aug. 4, 2021, issued in counterpart TW application No. 106139632. (8 pages).
First Office Action on CN Appl. No. 201780072289.X dated Nov. 23, 2021 (incl. full English translation) (23 pages).
International Preliminary Report on Patentability on International Application No. PCT/US2017/062460 dated Jul. 23, 2019 (6 pages).
International Search Report and Written Opinion on International Application No. PCT/US2017/062460 dated Jan. 22, 2018 (7 pages).
Notification of Reasons for Rejection on JP Appl. No. 2019-547584 dated Oct. 4, 2021 (18 pages, English translation included).

* cited by examiner (a)          (b)          (c)
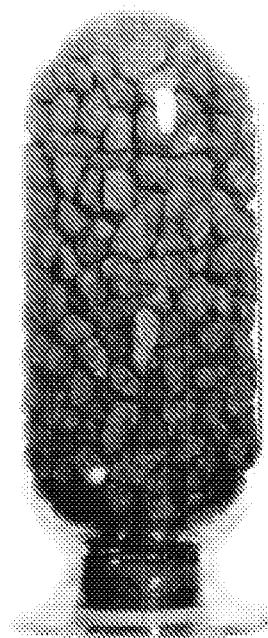 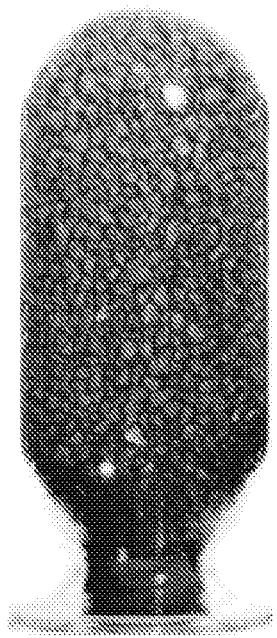 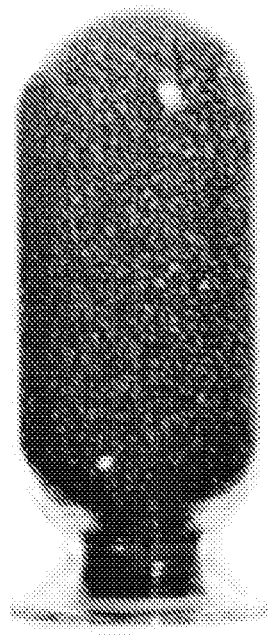

METHOD FOR MANUFACTURING CATALYSTS WITH REDUCED ATTRITION

CROSS REFERENCE TO RELATED APPLICATIONS

This application claims the benefit of the filing date of International Application No. PCT/US2017/062460 filed Nov. 20, 2017 and U.S. Provisional Patent Application No. 62/425,262 filed Nov. 22, 2016, entitled "METHOD FOR MANUFACTURING CATALYSTS WITH REDUCED ATTRITION", the disclosure of which is hereby incorporated by reference.

FIELD OF THE INVENTION

This invention relates to catalysts, and more particularly to a method for manufacturing the catalysts with reduced attrition.

BACKGROUND

Hydrogenation catalysts based on highly porous nickel materials are well known. Such materials are part of a family of metal alloy derived products sold by W. R. Grace & Co.-Conn. under the trademark "RANEY®." These porous materials, when microscopically viewed, take on a sponge-like appearance having tortuous pore channels throughout the nickel metal particles. Thus, such materials are generally viewed as porous or spongy metal alloy products.

The porous catalyst may be formed by using conventional metallurgical techniques to first form a precursor alloy of nickel and aluminum. The formed alloy is then crushed and/or ground and classified by passing it through a sieve to provide a material having a desired size. Larger particles exiting the crushing or grinding mechanism can be recycled for further size reduction.

The formed alloy is then subjected to an aqueous alkali (e.g., sodium hydroxide) solution to partially extract the aluminum metal from the alloy. The porous catalyst can be formed according to the process described in U.S. Pat. Nos. 1,628,190; 1,915,473; 2,139,602; 2,461,396; and 2,977,327. The teachings of these patents are incorporated herein in their entirety by reference.

Fixed Bed catalysts may be made by the conventional means of partial Al removal ('leaching') of large-granule alloys, with activity correlating to the extent of leaching. These catalysts generally have greater attrition when, all other things being equal, the extent of leaching (Al removal) is increased. This means that there is a limit to the activity achievable without the penalty of excessive attrition. Fixed bed catalysts are also liable to have high attrition values due to the relatively large size.

It is generally preferred that alloys having a higher Al content (lower Ni) are used to make fixed bed catalysts due to lower costs of these alloys. Kelley et al. (U.S. Pat. No. 4,247,722) also utilizes a catalyst comprising an alkali activated 42% nickel-58% aluminium alloy wherein at least 98% by weight of the nickel in the alloy is present as $NiAl_3$ for the hydrogenation of butadienepolyperoxide to 1,2- and 1,4-butanediol.

Fixed bed catalysts for hydrogenation, in addition to serving the main function of accelerating conversion of organic compounds to higher value ones, must survive handling and exposure to mechanical forces during use. The rate of attrition, i.e. loss of part of the large particles as they break into smaller ones, is important for the user. Higher attrition may lead to lower value catalysts due to reduction in flow (pressure drop) of the reactant/product stream as well as the problems created downstream by fine particles that escape the reactor. Commercial users of these catalysts prefer to avoid this breakage during loading of large column reactors for hydrogenation processes because this in turn prevents restricted flow ('pressure drop') and fines-loss problems which can shorten catalyst bed life or worsen net productivity.

BRIEF SUMMARY

Accordingly, one example of the present invention is an inventive method for manufacturing a catalyst using a higher Ni-content alloy, namely one that is significant more Ni-rich than those with the conventional 42% Ni. The inventive method includes providing alloy granules comprising aluminum and nickel, and treating the alloy granules with an alkaline solution to form the catalyst. A content of the nickel in the alloy granules may be within a range of about 43 wt % to about 60 wt %. The alloy granules may have effective diameters within a range of about 1 mm to about 10 mm.

Another example of the present invention is a catalyst comprising nickel and aluminum with reduced attrition. A content of the nickel in the catalyst may be within a range of about 57 wt % to about 75 wt %. The catalyst may have an effective diameter within a range of about 1 mm to about 10 mm and an attrition value of less than about 7.0%.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 shows alloy granules having different ranges of effective diameters (a) from about 3.3 to about 7 mm, (b) from about 2.4 to about 3.3 mm, and (c) from about 1.7 to about 2.4 mm.

DETAILED DESCRIPTION

The present invention is described with reference to embodiments of the invention.

The following terms, used in the present description and the appended claims, have the following definition:

The term "fixed bed" refers to a mass of catalyst which is packed in a constrained static bed within a catalytic reactor, and through which the reactant mixture moves continuously, as opposed to a stirred or fluidized bed ("slurry" system) which moves constantly within a reactor, along with the reactant mixture.

One example of the present invention is a method for manufacturing a catalyst using a higher Ni-content alloy, namely one that is significant more Ni-rich than those with the conventional 42% Ni. In one embodiment, the method includes providing alloy granules comprising aluminum and nickel. The content of the nickel in the alloy granules may be within a range of about 43 wt % to about 60 wt %, preferably about 45 wt % to about 58 wt %, more preferably about 50 wt % to about 56 wt %, and most preferably about 50 wt % to about 53 wt %.

In one embodiment, these alloy granules may be obtained by size reduction of larger alloy granules through crushing and/or grinding, and then classifying to provide alloy granules having a desired size. Crushing the alloy typically yields a broad distribution of granule sizes, and this distribution is narrowed in the classifying step by removing excessively large or excessively small granules, usually by sieving. Larger particles exiting the crushing or grinding mechanism can be recycled for further size reduction. These alloy granules may have irregular shapes. The term "effective diameter" of a granule formed by the crushing and or grinding method refers to a size of square openings in a standard sieve (U.S. or Tyler designation) having the largest mesh number through which the granule can pass. The granules have a distribution of effective diameters, whose range is determined by classifying through sieving steps. Specifically, first, the granules are sieved and passed through a lower mesh number standard sieve. Then, the granules which have passed are sieved, but retained by a higher mesh number standard sieve. The range of the effective diameters of the retained granules is determined to be from a size of the higher mesh number standard sieve to a size of the lower mesh number standard sieve.

In another embodiment, alloy granules of a desired size may be obtained by casting molten alloy in molds, pelleting, or forming droplets directly from the molten alloy in a cooling medium (gas or liquid). Methods of molding and pelleting may produce uniform alloy granules having a cylinder shape. The term "effective diameter" of a granule having a cylinder shape refers to the cross-sectional (circular) diameter of the cylinder. In one embodiment, spherical alloy granules may be formed by 'shotting' of molten alloy through rapid cooling. The term "effective diameter" of a granule having a sphere shape refers to the diameter of the sphere.

In one embodiment, the alloy granules may have effective diameters within a range of about 1 mm to about 10 mm, preferably about 2 mm to about 6 mm, and more preferably about 2.5 mm to about 5 man. In another embodiment, the overall granule size range may extend from an upper limit of a sieve designation of about '4' (~4.75 mm openings) which allows all of the utilized granules to pass through, to a lower limit of about '12' (~1.7 mm openings) through which essentially none of the utilized granules will pass. In other words, the alloy granules have effective diameters within a range of about 1.7 mm to about 4.75 mm. In another embodiment, the utilized granules may exist in a range of effective diameters that is a subset of this broadest overall range, e.g. from alloy designated as an '8-12 mesh' range which has essentially all of the particles smaller than 8 mesh (~2.4 mm) square openings and bigger than 12 mesh (~1.7 mm) openings. In other words, the alloy granules have effective diameters within a range of about 1.7 mm to about 2.4 mm. In another embodiment, the utilized granules may from alloy granules designated as a '4-8 mesh' range which has essentially all of the particles smaller than 4 mesh (~4.75 mm) square openings and bigger than 8 mesh (~2.4 mm) openings. In other words, the alloy granules have effective diameters within a range of about 2.4 mm to about 4.75 mm.

The alloy granules may then be treated or activated with an alkaline solution to form the catalyst. During the activation, the aluminum may be partially leached from the alloy granules by the alkaline solution to the extent of leaching at least 20%, preferably at least 30%, and more preferably at least 40% of the aluminum (Al) originally present. The upper limit of the Al leaching range varies for specific uses of the catalyst, and depends on the balance of opposing goals: higher activity (requiring higher leaching) vs. minimized attrition. The alkaline solution may be from either an inorganic or organic compound. In one embodiment, the alkaline solution comprises sodium hydroxide. A concentration of the sodium hydroxide in the alkaline solution may be within a range of 1 wt % to 20 wt %, preferably 1 wt % to 15 wt %, and more preferably 1 wt % to 10 wt %. The alloy granules may be treated with the alkaline solution at a temperature within a range of about 20° C. to about 110° C., preferably about 30° C. to about 90° C., and more preferably about 40° C. to about 70° C.

The process of treating the alloy granules by the alkaline solution is not limited. In one embodiment, the alloy granules being processed for fixed bed catalysts may sit in a vessel through which the alkaline solution is pumped and/or re-circulated. The aluminum contained in the alloy dissolves to form an alkali metal aluminate (e.g., sodium aluminate) with vigorous evolution of hydrogen. The granules and alkaline solution are normally allowed to remain in contact with each other for up to several hours at elevated temperature (e.g., 40°-60° C.) until the aluminum content is reduced to the desired level.

The alkaline solution may be introduced as a single solution, as a series of solutions of increasing strength over time, or instead as a solution whose strength is continuously varied over time by addition of extra NaOH to an existing reservoir that had contained the original weakest solution. In one embodiment, the alloy granules may be treated by an excess of NaOH solution at 3-10 wt %, circulated continuously through the bed of alloy granules while maintaining a temperature of 40-60° C.

In another embodiment, the alloy granules are first treated by a low concentration such as 3-4 wt % of NaOH solution for about 10 to 20 minutes. Then, additional sodium hydroxide may be slowly added into the solution to increase the concentration of the NaOH solution, for example, to a 6-8 wt % during a period of 20 to 30 minutes. Finally, the alloy granules are further treated by the increased concentration of the NaOH solution for another about 20 to 30 minutes.

After some designated time, the activation process is discontinued. The catalyst after activation may be separated from the reaction liquor and then washed with water until the wash water has a slightly alkaline pH value of about 8 to 9. The pore volume, pore size and surface area of the catalyst will depend upon the amount of aluminum in the initial alloy and the degree of leaching.

The method for manufacturing the catalyst may further comprise a step of promoting the catalyst. The catalyst may be promoted with from about 0.1% to about 15% by weight of a promoter transition metal, depending on the specific promoter metal. Such transition metals may include those capable of promoting the hydrogenation performance of the nickel catalyst, e.g. selectivity, conversion rate and stability against deactivation. In one embodiment, the catalyst preferably has a promoter transition metal content in the range of about 0.1 to about 10%, preferable about 0.5 to about 5.0% by weight.

The promoter transition metals may be added to the catalyst as a component in the base alloy of nickel and aluminum, but could also be added in the leaching solution used to remove aluminum from nickel aluminum alloy, or in an impregnation or coating bath following activation. In one embodiment, if added via the leaching solution, one can include therein, an amount of promoter precursor, e.g., chromium chloride or other Cr compound equivalent, to a metal: catalyst ratio of about 0.2 to 2% by weight, preferably 0.5 to 1.5% by weight. In one embodiment, the catalyst may be promoted by treating the catalyst with a solution comprising a soluble salt of a metal selected from the group consisting of Mo, Cr, W, Cu, and Fe, or mixtures thereof. In one embodiment, the catalyst may be promoted by Mo using a soluble Mo salt, such as ammonium heptamolybdate tetrahydrate $(NH_4)_6Mo_7O_{24}\cdot 4H_2O)$, circulated through the catalyst bed, then washed further with water. In another embodiment, the catalyst may be promoted by adding a component chosen from Mo, Cr, W, Fe or mixtures thereof in forming the alloy granules.

When using the option of applying promoters to the surface of the catalyst after activation, surface deposition may be conducted during a post-activation washing stage wherein the catalyst is contacted with a (usually alkaline-pH) salt solution, to achieve the same approximate ranges of promoter described above. This surface deposition can be done at a chosen pH in e.g. the range of 8-12, preferably 9-11. The catalyst is stored under water at an alkaline pH of usually 9-11. In another post leaching process, the metal can be plated onto the catalyst utilizing coating or plating techniques described in the U.S. Pat. No. 7,375,053, the contents of which are incorporated herein by reference.

In one embodiment, a content of the nickel in the catalyst may be within a range of about 57 wt % to about 75 wt %, preferably about 60 wt % to about 70 wt %. In another embodiment, the catalyst may have an attrition value of less than about 7.0%, preferably less than about 5.0%, and more preferably less than about 3.0%.

As a result of using a higher Ni content Ni-Ai alloy, namely one that is significant more Ni-rich than those with the conventional 42% Ni, the formed catalyst may have significantly reduced tendency to suffer attrition, the breaking of larger particles into smaller particles during handling and usage. Without being held to a particular theory, we believe that, in comparison to leaching conventional lower-Ni alloys to make catalysts, the leaching from the more Ni-rich alloys may lead to less collapse and less internal rearrangement of the original structure of the alloy particle, and thus to less inherent weakness against impacts, i.e. improved attrition resistance.

Another example of the present invention is the catalyst formed by the inventive method comprising treating granule alloys having a high nickel-content with an alkaline solution. The catalyst may be used partly or wholly as a fixed bed sponge metal catalyst for a hydrogenation process. The catalyst may also be used in a process for hydrogenation, e.g. specifically in a process for producing 1,4 butanediol by hydrogenation or a process for producing sorbitol by hydrogenation of glucose.

The above catalysts may be more efficiently utilized in continuous processes, including those using a fixed catalyst bed. A trickle-bed process can be used with a fixed catalyst bed. The catalysts utilized in conventional fixed bed processes can be in various forms, including, but not limited to, granules, spheres, pressed cylinders, tablets, lozenges, wagon wheels, rings, stars, or extrudates, such as solid extrudates, polylobal extrudates, hollow extrudates and honeycomb bodies.

Hereinafter, the present invention will be described in more detail with reference to Examples. However, the scope of the present invention is not limited to the following Examples.

EXAMPLES

The methods for alloy forming and sizing, catalyst attrition testing, and catalyst activity testing are described first and are applied uniformly to all subsequent examples.

Forming and Sizing of Alloy Particles

Nickel-Aluminum alloy slabs were formed by conventional melting and casting methods described previously. This was followed by breaking of the slabs of the cast alloy into smaller granules (using a Bico-Braun Intl. jaw crusher with ~¼ jaw opening setting). The granules (particles) at this stage have an excessively broad distribution. In the sieving step that followed next, first, the granules are sieved and passed through a lower mesh number standard sieve. Then, the granules which have passed are sieved, but retained by a higher mesh number standard sieve. The range of the effective diameters of the retained granules is determined to be from a size of the higher mesh number standard sieve to a size of the lower mesh number standard sieve. FIG. 1 shows alloy granules having different ranges of effective diameters (a) from about 3.3 to about 7 mm, (b) from about 2.4 to about 3.3 mm, and (c) from about 1.7 to about 2.4 mm. These alloy granules were classified by (a) 3-6 mesh, (b) 6-8 mesh, and (c) 8-12 mesh standard sieves, respectively.

In the subsequent Examples and Comparative Examples, the alloy granules (c) were used. These alloy granules passed through an 8 mesh standard sieve, but were retained (did not pass through) by a 12 mesh sieve just below the 8 mesh sieve, in treatment for 1 minute in a sieve-shaker (Rotap®).

A relationship of the sieve designation and nominal sieve opening is shown in Table 1 below, which is Obtained from the Aldrich 2003-2004 Catalog/Handbook of Fine Chemicals.

TABLE 1

Relationship of the sieve designation and nominal sieve opening.

| Sieve Designation | | Nominal Sieve Opening | | |
|---|---|---|---|---|
| Standard | Mesh | Inches | mm | Microns |
| 5.66 mm | No. 3 ½ | 0.223 | 5.66 | 5660 |
| 4.76 mm | No. 4 | 0.187 | 4.76 | 4760 |
| 4.00 mm | No. 5 | 0.157 | 4.00 | 4000 |
| 3.36 mm | No. 6 | 0.132 | 3.36 | 3360 |
| 2.83 mm | No. 7 | 0.111 | 2.83 | 2830 |
| 2.38 mm | No. 8 | 0.0937 | 2.38 | 2880 |
| 2.00 mm | No. 10 | 0.0787 | 2.00 | 2000 |
| 1.68 mm | No. 12 | 0.0661 | 1.68 | 1680 |
| 1.41 mm | No. 14 | 0.0555 | 1.41 | 1410 |
| 1.19 mm | No. 16 | 0.0496 | 1.19 | 1190 |
| 1.00 mm | No. 18 | 0.0394 | 1.00 | 1000 |
| 841 µm | No. 20 | 0.0331 | 0.841 | 841 |

Attrition Testing of Activated Catalyst

The tendency of the catalyst to break into smaller particles under mechanical stresses was measured in a simple roller-mill device, consisting of a capped polyethylene bottle ("16 oz. poly wide mouth bottle with baffles, FAB", available from Fisher Scientific), inside a cylindrical metal "mill jar" sleeve (part 000-264 from Advanced Ceramics Manufacturing), which was rotated at 100 RPM on the paired rollers of a 'Model JRM' from Paul O. Abbe, Inc., a machine typically used as a ball mill. The catalyst sample of 100 g was immersed in water in the capped bottle in each test. The residence time in this attrition test was 20 minutes. The amount of fine particles in the catalyst sample was determined by weighing, done both before and after the 20 minute roller mill step. The fines fraction was separated from the main sample using a standard 12 mesh sieve shaken mechanically for 2 minutes on a Rotap® shaker. Fines separated in the sieving before the attrition test were recombined with the main sample before continuing with the roller mill test and second sieving. The amount of attrition for each test was defined as the after—before difference in weighed fines content, the portion of catalyst passing through a 12-mesh sieve (~1.7 mm opening), expressed as a percentage of original sample weight: % attrition=[% under 12 mesh after test]−[% under 12 mesh before test].

Catalyst Activity Testing

Catalyst activity was measured in a fixed bed hydrogenation reactor using conversion of dextrose (glucose) solution to sorbitol as the performance criterion.

A vertical column fixed bed reactor with an internal diameter of ½ inch and a working bed length of 6 inches was used, with a central ⅛ inch diameter thermocouple well. Working volume of the catalyst bed was 18 cc (mL). Catalyst was loaded into this column reactor under water, which was subsequently pushed out of the catalyst bed zone by flowing nitrogen and then hydrogen, after connection of the modular catalyst bed section into the main reactor piping system.

A 40% aqueous solution of crystalline dextrose in water was pumped from an external feed tank to the fixed bed reactor maintained at 120° C. Simultaneously, hydrogen gas was delivered through the catalyst bed at 500 mL/minute flow rate and 1000 psig pressure (68 atm.). The liquid flow rate was maintained successively in multiple experimental runs at three different levels: 0.20, 0.23 and 0.25 mL/minute. This is a means of discriminating among catalysts of similar activities, based on ability to achieve high conversion of the feed to product at the highest possible flow rate.

Product samples were collected for each 4 hours of run time. Residual dextrose (unconverted feed) was determined by analysis with a "Hemocue Glucose 201 Analyzer" available from Fisher Scientific. Product samples were diluted with water to allow for detection in the optimum instrument response range for the colorimetric slides provided. This yields the weight percentage dextrose in the product sample.

Percentage conversion of the dextrose was defined as:

100%−2.5*(wt % dextrose)

where wt % dextrose is the residual amount in the product, as determined above, and the 2.5 factor accounts for the 40% feed concentration. The conversion values as obtained above were averaged for 3 segments of 4 hours each at a given liquid feed flow rate.

HPLC analysis of the product samples was performed separately to confirm accuracy of the Hemocue instrument for dextrose content. Conditions used for the HPLC were: Rezex RCM monosaccharide Ca+2 column (ser. no. 735463-1), dimensions 300×7.8 mm; Rezex RCM monosaccharide Ca+2 column guard (ser. no. 728606-3), dimensions 5×7.8 mm; 0.7 mL/minute flow; D.I. water as eluent; Gradient: isocratic; 10 uL injection; RI detector, 35 minute run time.

The main by-product, mannitol, was found to be in a range of 0.4 to 0.7 wt % for all subsequent experimental catalysts.

Comparative Example 1

Catalyst Activation

A 42% Ni-58% Al alloy, made by conventional melting and mixing techniques, was crushed and sieved to 8-12 mesh size range (~2-3 mm particle diameters). To activate this alloy into a catalyst by Al leaching, 680 g of this 8-12 mesh alloy was placed in a 4 liter beaker, through which 8.1 liters of a 3% aqueous NaOH solution was then recycled, using a pump between the beaker and an external reservoir holding the excess NaOH solution. This first condition (stage 1) was continued for 10 minutes, maintaining temperature in the leaching beaker at 45° C. by use of cooling coils in the beaker. For the next 20 minutes (stage 2) a solution containing an additional 288 g of (pure solid) NaOH and 462 g of water was steadily and continuously added to the reservoir to finally increase the NaOH input from initial 3% concentration to an equivalent of initial 6% NaOH (i.e. ignoring the amount consumed by the Al-leaching reaction). After this addition of NaOH, the system was held at the same temperature and liquid flow conditions for 20 more minutes (stage 3).

The catalyst was then washed with 5 Liters of a 2% NaOH solution for 10 minutes, then with water at 45° C. until the effluent wash water reached an interim pH of 10. Molybdenum promoter was added to the catalyst using 20.5 g of ammonium heptamolybdate (NH4)6Mo7O24·4H2O in 70 g of water. The Mo-containing solution was then stirred to distribute it through the catalyst bed for 60 minutes. The catalyst was then further washed with water to a pH of 9.

The final composition of the catalyst as measured by ICP chemical analysis was 54.9% Ni, 43.3% Al and 1.6% Mo, which equates to leaching (removal) of 43% of the initial aluminum in the alloy.

The catalyst in Comparative Example 1 had 10.2% attrition, representing the baseline extent of breakage for conventional catalyst. The % conversions of dextrose at the 3 programmed feed flow rates for this catalyst were:
99.9% conversion at 0.20 mL/min flow rate
99.9% conversion at 0.23 mL/min flow rate
99.3% conversion at 0.25 mL/min flow rate This combination of high activity but also excessive attrition (about 10%) represents the status to be improved upon in previously existing catalysts.

Comparative Example 2

A catalyst was prepared from 58% Al, 42% Ni alloy similarly to the method of Comparative Example 1 above, with these differences:
a) the added NaOH in Stage 2 was in the amount of 465 g solid NaOH dissolved in 285 g of water. This increased the total input of NaOH to the equivalent of 8% starting concentration (vs. 6% for Comparative Example 1).
b) After the 20 minute addition time of Stage 2, the mixture was held at existing conditions with circulation of liquid for 10 minutes, shorter duration than the 20 minutes in Comparative Example 1.

The resulting catalyst analysis by ICP indicated 49.8% Ni, 49.0% Al, and 1.1% Mo, corresponding to leaching of only 29% of initial Al vs. the 45% of Comparative Example 1. The attrition level from the above described method was 8.6%, a small improvement on the 10.2% baseline.

The % dextrose conversions for catalyst of comparative Example 2 were:
99.5% conversion at 0.20 mL/min flow rate;
96.5% conversion at 0.23 mL/min flow rate;
96.3% conversion at 0.25 mL/min flow rate;

Both activity and attrition were decreased as a result of the lower level of leaching of Al compared to baseline of Comparative Example 1, but this trade-off is still undesirable in that the activity has suffered noticeably without significant improvement in attrition.

Example 1

A catalyst was prepared by a process similar to that of comparative Example 1, but with changes and details as noted:

a) from an alloy having 53% Ni and 47% Al. The alloy weight employed was 500 g;
b) the initial 3% leaching solution had a volume of about 6 liters;
c) The timing of Stages 1, 2 and 3 was 10, 20, and 20 minutes, respectively, as in Comparative Example 1. Temperature was 45° C. as in Comparative Examples 1 and 2;
d) The amount of NaOH used in increasing the input concentration to equivalent of about 6% in Stage 2 was 212 g solid NaOH, dissolved in 340 g of water; and
e) Molybdate salt addition: 15.1 g of ammonium heptamolybdate.

Resulting catalyst had this assay by ICP analysis: 68.5% Ni, 28.8% Al, and 1.6% Mo, corresponding to 53% Al removal. Attrition testing showed a much lower result of 2.7%, about one quarter of the baseline Comparative Example 1.

Activity testing for the catalyst of Example 1 resulted in:
96.4% conversion at 0.20 mL/min flow rate;
93.6% conversion at 0.23 mL/min flow rate;
95.4% conversion at 0.25 mL/min flow rate;

Example 2

Compared to Example 1, the modifications made in this catalyst preparation were:
a) The activation temperature was maintained at 60° C., increased from 45° C.;
b) The % NaOH input was raised from initial 3% to 8% by addition of a mixture of 342 g solid NaOH and 209 g water in stage 2;
c) The duration of Stages 1, 2 and 3 were 10, 12 and 17 minutes respectively; and
d) At the end of Stage 3, the used leaching solution was removed from the reactor+reservoir and replaced with 6.5 liters of 10% NaOH solution which was recirculated through the catalyst bed at 60° C. for 12 additional minutes.

The resulting catalyst analysis by ICP yielded 65.4% Ni, 32.5% Al, and 1.5% Mo. This amounts to leaching of 44% of original Al. Attrition testing showed an improved result of 2.6%, comparable to Comparative Example 1.

Activity testing for the catalyst of Example 2 resulted in:
99.4% conversion at 0.20 mL/min flow rate
99.0% conversion at 0.23 mL/min flow rate
98.8% conversion at 0.25 mL/min flow rate Example 3

This catalyst preparation involved only one change from Example 2: substitution of a 50% Ni, 50% Al alloy for the 53% Ni, 47% Al alloy.

The resulting catalyst analysis by ICP yielded 61.1% Ni, 37.2% Al, and 1.4% Mo. This amounts to leaching of 39% of original Al.

The selective removal of 39% of the original aluminium reduces the weight of the alloy by 0.391×50% or 19.56% overall (i.e. 19.56 g out of each 100 g, e.g.). Addition of the Mo promoter increases the weight by 1.15 g per 100 g of original alloy. Renormalizing the catalyst assay is equivalent to dividing the wts. of each component by the new total catalyst weight of 1.15+(100−19.44), or 81.71.

Thus, final % Al is (100%)*(50−19.44)/81.71=37.3%;
final % Ni is (100)*50/81.71=61.2%; and
final % Mo is (100%)*1.15/81.71=1.4%.

Attrition testing showed a result of 5.4%, or about ½ of that of the prior art baseline of comparative Example 1.

Activity testing for Example 3 catalyst resulted in:
99.8% conversion at 0.20 mL/min flow rate
99.5% conversion at 0.23 mL/min flow rate
99.6% conversion at 0.25 mL/min flow rate Examples 2 and 3 achieved the best balance of high activity (conversion of dextrose) and low attrition.

The complete results are shown in Table 2 below.

TABLE 2

| Parameter/Output | Catalyst Example No. | | | | |
| --- | --- | --- | --- | --- | --- |
| | Comparative Example 1 | Comparative Example 2 | Example 1 | Example 2 | Example 3 |
| alloy % Ni | 42 | 42 | 53 | 53 | 50 |
| activn temp (deg C.) | 45 | 45 | 45 | 60 | 60 |
| activn % NaOH ramp | 3 --> 6 | 3 --> 8 | 3 --> 6 | 3 --> 8, +10 | 3 --> 8, +10 |
| times (min.), stages 1, 2, 3 | 10, 20, 20 | 10, 20, 10 | 10, 20, 20 | 10, 12, 17 (+12) | 10, 12, 17 (+12) |
| % of alloy Al leached | 43 | 29 | 53 | 44 | 39 |
| final catalyst % Ni | 54.9 | 49.8 | 68.5 | 65.4 | 61.1 |
| final catalyst % Al | 43.3 | 49.0 | 28.8 | 32.5 | 37.2 |
| final catalyst % Mo | 1.6 | 1.1 | 1.6 | 1.5 | 1.4 |
| % conversion at 0.20 mL/min flow | 99.9 | 99.5 | 96.4 | 99.4 | 99.8 |
| % conversion at 0.23 flow | 99.9 | 96.5 | 93.6 | 99.0 | 99.5 |
| % conversion at 0.25 flow | 99.3 | 96.3 | 95.4 | 98.8 | 99.6 |
| % attrition (change in −12 mesh) | 10.2 | 8.6 | 2.7 | 2.6 | 5.4 |

The invention claimed is:

1. A method for manufacturing a catalyst, comprising providing alloy granules comprising aluminum and nickel, and treating the alloy granules with an alkaline solution comprising 1 wt % to 20 wt % sodium hydroxide to form the catalyst, wherein a content of the nickel in the alloy granules is 53 wt % to 60 wt %, wherein at least 40% of the aluminum from the alloy granules is leached upon treating with the alkaline solution, wherein the catalyst exhibits an attrition value of less than 5.0%, and wherein the catalyst comprises nickel and aluminum, and wherein a content of the nickel in the catalyst is about 57 wt % to about 75 wt %.

2. The method of claim 1, wherein the alloy granules have effective diameters within a range of about 1 mm to about 10 mm.

3. The method of claim 1, wherein the content of the nickel in the alloy granules is 53 wt %.

4. The method of claim 1, wherein the content of the nickel in the alloy granules is 53 wt % to 56 wt %.

5. The method of claim 1, wherein the alloy granules have effective diameters of about 2 mm to about 6 mm.

6. The method of claim 1, wherein a concentration of the sodium hydroxide in the alkaline solution is 1 wt % to 15 wt %.

7. The method of claim 1, wherein a concentration of the sodium hydroxide in the alkaline solution is 1 wt % to 10 wt %.

8. The method of claim 1, wherein the alloy granules are treated with the alkaline solution at a temperature of about 20° C. to about 110° C.

9. The method of claim 1, further comprising promoting the catalyst using an additional process step chosen from:
   a. treating the catalyst with a solution comprising a soluble salt of a metal selected from the group consisting of Mo, Cr, W, Cu, Fe, and mixtures of any two or more thereof, or
   b. adding a component chosen from Mo, Cr, W, Cu, Fe, and mixtures of any two or more thereof in forming the alloy granules.

10. The method of claim 1, wherein a content of the nickel in the catalyst is about 60 wt % to about 70 wt %.

11. The method of claim 1, wherein the catalyst exhibits an attrition value of 3.0% or less.

12. The method of claim 1, wherein a concentration of the sodium hydroxide in the alkaline solution is from 6 wt % to 15 wt %.

\* \* \* \* \*